United States Patent [19]

Loibner et al.

[11] Patent Number: 4,503,046

[45] Date of Patent: Mar. 5, 1985

[54] 1-NITRO-AMINOGLYCOSIDE DERIVATIVES, PHARMACEUTICAL COMPOSITIONS CONTAINING THEM AND SUCH DERIVATIVES FOR USE AS PHARMACEUTICALS

[75] Inventors: Hans Loibner; Wolfgang Streicher; Peter Stütz, all of Vienna, Austria

[73] Assignee: Sandoz Ltd., Basel, Switzerland

[21] Appl. No.: 404,817

[22] Filed: Aug. 3, 1982

[30] Foreign Application Priority Data

Aug. 7, 1981 [CH] Switzerland .......................... 5107/81

[51] Int. Cl.³ ...................... A61K 31/71; C07H 15/22
[52] U.S. Cl. ...................................... 514/40; 536/13.6; 536/16.6; 536/16.8; 536/17.7
[58] Field of Search ................... 536/13.6, 16.6, 16.8, 536/17.7; 424/180

[56] References Cited

U.S. PATENT DOCUMENTS

| | | | |
|---|---|---|---|
| 4,062,947 | 12/1977 | Wright et al. | 536/13.6 |
| 4,085,208 | 4/1978 | Mallams et al. | 536/13.6 |
| 4,224,315 | 9/1980 | Stadler et al. | 536/13.6 |

OTHER PUBLICATIONS

Baer et al., "Can. Jour. Chem.", vol. 52, No. 12, Jun., 1974, pp. 2257-2267.
Migrdichian, "Organic Synthesis", Reinhold Publishing Corp., New York, 1957, pp. 465-467 and 473.
Rinehart, Jr. et al., Amer. Chem. Soc. Symposium Series 125, Washington, D.C., 1980, pp. 1-11.

Primary Examiner—Johnnie R. Brown
Attorney, Agent, or Firm—Gerald D. Sharkin; Richard E. Vila; Frederick H. Weinfeldt

[57] ABSTRACT

Hydroxymethylated aminoglycoside derivatives which are useful, in particular as anti-bacterially active antibiotics.

10 Claims, No Drawings

1-NITRO-AMINOGLYCOSIDE DERIVATIVES, PHARMACEUTICAL COMPOSITIONS CONTAINING THEM AND SUCH DERIVATIVES FOR USE AS PHARMACEUTICALS

The present invention concerns aminoglycoside derivatives processes for their production, pharmaceutical compositions containing them and such derivatives for use as pharmaceuticals.

In particular the invention concerns compounds of formula I

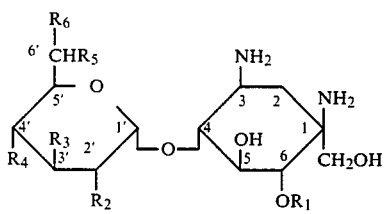

wherein $R_1$ represents hydrogen or a group of formula

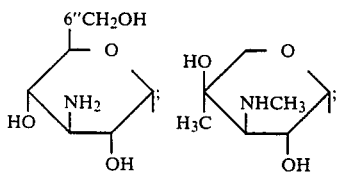

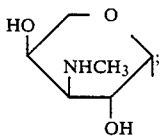 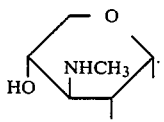

$R_2$ represents hydroxy or amino,
$R_3$ represents hydrogen or hydroxy,
$R_4$ represents hydrogen or hydroxy,
$R_5$ represents amino, methylamino, dimethylamino or, when $R_2$ represents amino also hydroxy and
$R_6$ represents hydrogen or methyl in free base form or in the form of an acid addition salt.

According to the invention these compounds can be prepared
(b) by reducing a compound of formula III

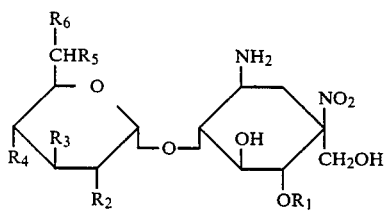

wherein $R_1$ to $R_6$ are as defined above, and amino groups, where present, may be protected, and if required deprotecting any protected amino groups still present in the compound thus obtained, or (b) to produce a compound wherein $R_5$ represents methylamino or dimethylamino, mono- or di-methylating a corresponding compound of formula I wherein $R_5$ represents amino or mono-methylating a corresponding compound wherein $R_5$ represents methylamino, whereby other amino groups, where present may be protected, and if required deprotecting any protected amino groups in the compound thus obtained; and recovering the compound of formula I thus obtained in free form or in the form of an acid addition salt as required.

Process (a) can be carried out in a manner conventional for such reductions such as described in Houben-Weyl Bd. 4/Ic, for example, using Raney-Nickel and hydrogen in an inert solvent such as an alcohol e.g. methanol. Raised pressure can be advantageous.

Process (b) can be effected using conventional methylating agents. For example for introduction of a single methyl group in a compound containing a $6'$—$NH_2$ group this is first reacted selectively with a carbonic acid derivative of formula X—$COOR_7$ wherein X represents a reactive group and $R_7$ represents alkyl or aralkyl to produce the corresponding $NHCOOR_7$ derivative which is then reduced in conventional manner, e.g. with a complexmetal hydride e.g. LiAlH$_4$. Introduction of two methyl groups in compounds containing a $6'$—$NH_2$ group can for example be carried out by protecting all amino groups except that at $6'$-, introducing methyl groups in conventional manner e.g. by reaction with formaldehyde in the presence of a reducing agent or of $NaH_2PO_3$ and then deprotecting the end product. Introduction of a further methyl group in a $6'$-methylamino compound may be effected analogously in conventional manner.

Suitable protecting groups are for example benzyloxycarbonyl, tert.butoxycarbonyl or trichlorethoxycarbonyl. These groups can be introduced and removed in conventional manner such as for example analogously to the methods described hereinafter in the examples.

The compounds of the formula I may be converted in conventional manner into their acid addition salts and vice versa.

The starting materials of formula III can be prepared by reacting a compound of formula IV

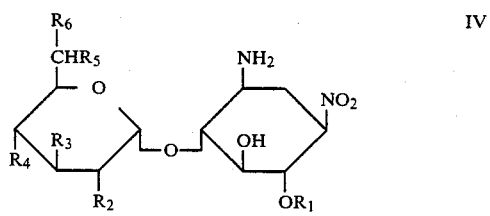

wherein $R_1$ to $R_6$ are as defined above, and amino groups, where present, may be protected, with formaldehyde and optionally deprotecting any protected amino groups in the compound thus obtained.

This reaction may be carried out in conventional manner in a solvent inert under the reaction conditions e.g. a lower alcohol such as methanol or a chlorinated hydrocarbon such as chloroform and in the presence of a base such as a tertiary amine e.g. triethylamine. Temperatures conveniently lie between room temperature and the boiling point of the reaction mixture. The compounds thus obtained can, of course, be further reacted directly e.g. in situ according to process (a). Direct further reaction is preferred.

The compounds of formula IV can be obtained by oxidising a compound of formula V $$V$$

wherein $R_1$ to $R_6$ are as defined above,
and all amino groups, with the exception of that in position 1, are protected. This oxidation can take place in conventional manner e.g. as described in J.Org.-Chem. 44/659 (1979) or with $KMnO_4$. Once again the resulting products may optionally be deprotected or, preferably, directly reacted further to compounds of formula III.

The compounds of the formula V are known, can be obtained as referred to in the literature (cf. Merck Index 4th Edition, pp. 565 and 692) or are available commercially. They can be employed in the form of mixtures such as those obtained when preparation is by fermentative methods (e.g. gentamicin $C_2/C_{2a}$-4/1 to 3/2). Reaction of these compounds will lead in turn to mixtures of compounds IV, III or I respectively. Such mixtures can be separated into their individual components at any stage of the preparative chain, but this is preferably carried out on deprotected end products of formula I. The methods employed in separation are conventional such as described in U.S. Pat. No. 3,984,395 or K. Byrne et. al. J.Chromatogr. 131/191 (1977).

The compounds of formulae III and IV are new and also form part of the invention.

All intermediate and end products can be isolated and purified according to known methods.

The compounds of formula I exhibit chemotherapeutic activity. In particular they exhibit antimicrobial activity as indicated in vitro in series dilution tests and in vivo in tests on mice using various bacterial strains such as e.g. *Staph. aureus, Staph. epidermis,* Haemophilis spp., *Pseudomonas aeruginosa, E. coli, Proteus vulgaris, Proteus mirabilis, Proteus morganii, Enterobacter cloacae, Klebsiella pneumonias* and *Serratia marcescens.* This activity is observed in vitro at concentrations between ca. 0.05 to 50 μg/ml and in vivo at between ca. 0.4 and 100 mg/kg animal body weight. They are particularly effective in aminoglycoside resistant strains and have thus a broad spectrum of activity.

The compounds are therefore useful as antibacterially active antibiotics.

For this use, the effective dosage will, of course, vary depending on the particular compound employed, the mode of administration and the treatment desired. However, in general, satisfactory results can be obtained when the compounds are administered at a daily dosage of from about 2 to 30 mg/kg of animal body weight, suitably given in divided doses two to four times daily. For most large mammals, the total daily dosage is from about 0.1 to 2 g and dosage forms suitable for internal administration comprise about 25 to 1500 mg of the compound in admixture with a solid or liquid pharmaceutical carrier or diluent.

The compounds may be used in free base form or in the form of chemotherapeutically acceptable acid addition salts e.g. as the penta hydrochloride. Such salt forms exhibit the same order of activity as the free base forms.

The compounds of formula I may be administered in similar manner to known standards for use in such indications e.g. gentamicin.

The suitable daily dosage for a particular compound will depend on a number of factors such as its relative potency of activity. It has for example been determined in vitro tests on aminoglycoside resistant strains such as e.g. *E. coli, Pseudomonas aeruginosa* and *Proteus mirabilis* that the preferred compound of the invention 1-C-hydroxymethylgentamicin $C_2$.pentahydrochloride has activity in the range of 0.1 to 3 μg/ml compared with 0.1 to 100 μg/ml for gentamicin. It is therefore indicated that the compounds be administered at similar or lower dosages than conventionally employed for gentamicin.

The compounds may be admixed with conventional chemotherapeutically acceptable diluents and carriers, and, optionally, other excipients and administered in such forms as tablets, capsules or injectable preparations.

Such compositions also form part of the invention.

The invention therefore also concerns a method of combatting bacteria comprising administering to a subject in need of such treatment an effective amount of a compound of formula I or a chemotherapeutically acceptable acid addition salt thereof and such compounds for use as chemotherapeutic agents, in particular antibacterially active antibiotics.

Preferred meanings for the substituents are
$R_1$ = (a) formula IIa; (b) formula II
$R_2$ = (a) hydroxy or amino; (b) amino
$R_3 + R_4$ = (a) hydrogen; (b) hydroxy
$R_5$ = (a) amino, methylamino, dimethylamino; (b) amino or when $R_2$ represents amino also hydroxy
$R_6$ = (a) hydrogen or amino; (b) hydrogen; as well as combinations of these.

A particular group of compounds according to the invention is that wherein
$R_1$ represents a group of formula IIa,
$R_2$ represents amino,
$R_3$ and $R_4$ represent hydrogen and
$R_6$ represent hydrogen or methyl and
$R_5$ represent amino, methylamino or dimethylamino.

Another interesting group covers those compounds wherein
$R_1$ represents a group of formula II,
$R_2$ represents hydroxy or amino,
$R_3$ and $R_4$ represent hydroxy,
$R_5$ represents amino or when $R_2$ represents amino also hydroxy and
$R_6$ represents hydrogen.

A particularly preferred single compound is 1-C-hydroxymethylgentamicin $C_2$ in free base form or acid addition salt form preferably pentahydrochloride or sulphate salt form.

The following examples illustrate the invention. All temperatures are in degrees centigrade.

EXAMPLE 1

1-C-Hydroxymethylgentamicin $C_2$.Pentahydrochloride (compound no. 1—process a))

0.64 g of 3,2',6',3''-Tetra-N-tert.-butoxycarbonyl-1-desamino-1-nitrogentamicin $C_2$ are dissolved in 5 ml of methanol and after cooling to $-7°$ reacted with 0.3 ml of triethylamine. After 5 mins the solution is poured into 10 ml of 37% formaldehyde solution and raised to room temperature. After dilution with water and acidification with 0.1N HCl the solution is extracted with dichloromethane and the organic phase concentrated on a rotary evaporator. The substance having $R_f=0.56$ (in dichloromethane/methanol=10/1) is isolated by chromatography on silica gel with dichloromethane/methanol (100/2-4). The resulting compound is reduced with hydrogen at 4 atm. using a Raney-Nickel suspension in 20 ml of methanol. After filtration of the catalyst the solution is concentrated on a rotary evaporator and the residue taken up with ethyl acetate, washed with 2N ammonia solution and concentrated on a rotary evaporator. This residue is taken up in 5 ml of trifluoroacetic acid and mixed after 3 minutes with 100 ml of diethylether. The precipitate is filtered off and converted to the (penta)hydrochloride using IRA 401 $R_f=0.53$ (dichloromethane/methanol/25% ammonia=2/2/1).
C-13 NMR: 102,8;96,0;85,8;78,0;73,2;70,7;69,8;68,9;67,0;64,1; 60,7;59,3;50,4;49,6;48,2;35,2;29,8;23,0;21,7;21,2;13,5.

EXAMPLE 2

1-C-Hydroxymethylgentamicin $C_{1a}$.Pentahydrochloride (compound no. 2—process a))

0.8 g of 3,2',6'3''-Tetra-N-tert.-butoxycarbonyl-1-desamino-1-nitrogentamicin $C_{1a}$ are dissolved in 20 ml of chloroform, reacted with 10 g of paraformaldehyde and 1 ml of triethylamine and refluxed for 30 minutes. The resulting mixture is filtered under suction and the mother liquor chromatographed over silica gel with ethylacetate/hexane (2/1). $R_f=0.5$ (in dichloromethane/methanol=9/1). The resulting product is reduced with hydrogen at 4 atm. using a Raney-Nickel suspension in 30 ml of methanol. Filtration of the catalyst yields an amorphous foam which is dissolved in 10 ml of trifluoroacetic acid and after 7 minutes added to 200 ml of diethylether. The precipitate is filtered under suction and chromatographed over silica gel with chloroform/methanol/30% ammonia (70/26/9). The product having $R_f=0.13$ in the above eluant is collected and converted by acidification with methanolic hydrochloric acid and precipitation with diethylether into the (penta)hydrochloride.

H-NMR, characteristic signals: 1,37 s,3H;2,72 dd,$J_1=14,J_2=3,5$,1H; 2.96 s,3H; 5,15 d,J=3,6,1H; 5,85 d,J=3,6,1H.

Anlogously to the above Examples 1 and 2 or as otherwise herein described, the following compounds may be obtained from the appropriate starting materials:

1-C-Hydroxymethylgentamicin $C_1$.pentahydrochloride (compound no. 3).
C-13 NMR: 103,1;95,5;86,1;77,6;73,7;71,1;70,3;69,1;67,5;64,7; 61,1;59,8;58,7;49,9;48,6;35,6;32,3;30,2;24,4;22,1;21,8;10,- 5.

1-C-Hydroxymethylgentamicin $C_{2a}$.pentahydrochloride (compound no. 4)

H-NMR, characteristic signals: 1,34 d,J=7,3H; 1,37 s, 3H;2,72 dd, $J_1=13,5,J_2=3,5$, 1H; 2.96 s, 3H;5,12 d,J=3,6, 1H;5,91 d,J=3,6,1H.

1-C-Hydroxymethylgentamicin C.pentahydrochloride (compound no. 5).

1-C-Hydroxymethylgentamicin $C_2/C_{2a}$.pentahydrochloride (compound no. 6)

Compound no. 6 is obtained from starting materials themselves derived from fermatatively produced gentamicin $C_2/C_{2a}$ (ca 4/1) and can be resolved as follows:

300 mg of 1-C-Hydroxymethylgentamicin $C_2/C_{2a}$.pentahydrochloride are dissolved in water and this solution introduced onto a middle pressure column (1.5 m×1.6 cm) filled with CG 50 I($NH_4^+$-form). Elution with ca 1 liter of water follows (flow 20 ml/minute, pressure 4–5 bar). This is followed by gradient elution over 90 minutes from water to 0.4N ammonia. The fractions containing the product are concentrated individually on a rotary evaporator. The first 5 fractions contain according to 250 Mhz H-NMR the desired $C_2$ derivative in 95% purity.

EXAMPLE 3

1-C-Hydroxymethyl-6'-N-methylgentamicin $C_{1a}$.pentahydrochloride (compound no. 7—process b))

1.63 g of 1-C-Hydroxymethylgentamicin $C_{1a}$ (free base) are dissolved in 30 ml of methanol and a solution of 1.06 g of N-benzyloxycarbonyloxy-5-norbornene-2,3,-dicarboxylic acid imide in 20 ml of methanol and 5 ml of dichloromethane added at $-20°$. After 1 hour the mixture is concentrated on a rotary evaporator and the residue chromatographed on silica gel with chloroform/methanol/25% ammonia (15/4/1). The product with $R_f=0.45$ (in chloroform/methanol/30% ammonia=70/21/9) is collected. 250 mg of the 1-C-hydroxymethyl-6'-N-carbobenzoxygentamicin $C_{1a}$ thus obtained are dissolved in 25 ml of abs. tetrahydrofuran and under an argon atmosphere lithium aluminum hydride added until gas evolution ceases. The mixture is then refluxed for 1 hr. The excess reducing agent is destroyed with methanol and the reaction mixture acidified with acetic acid, the precipitate filtered off and the clear filtrate concentrated on a rotary evaporator. The residue is dissolved in 10 ml of water and then eluted over CG 50I($NH_4^+$-form) initially with water and then gradually with water to 0.5N ammonia.

The fractions containing the product are concentrated, the residue dissolved in methanolic hydrochloric acid and the title product precipitated with diethylether $R_f=0.2$ (in chloroform/methanol/30% ammonia=70/26/9).

H-NMR, characteristic signals: 1,35 s,3H; 2,70 dd,$J_1=14,J_2=3,5$,1H;2,78 s, 3H;2,95 s,3H;5,12 d,J=3,6,1H;5,84 d,J=3,6,1H.

EXAMPLE 4

1-C-Hydroxymethyl-6'-N-dimethylgentamicin $C_{1a}$.sulphate (compound 8—process b))

400 mg 1-C-Hydroxymethyl-6'-carbobenzoxygentamicin $C_{1a}$ are dissolved in 10 ml of methanol and 900 mg of di-tert.-butyldicarbonate and 0.2 ml of pyridine added. The mixture is stirred for 2 days at room temperature and then refluxed for 3 hrs. Concentration on a rotary evaporator is carried out followed by dissolution of the residue in diethylether and threefold trituration with 2N ammonia. The organic phase is concentrated, dissolved in 10 ml of methanol, mixed with 500 mg of ammonium formate, 2 ml of water and 100 mg palladium 10% on charcoal and refluxed for 15 minutes. Extraction by shaking with water and ethylacetate follows and the resulting ethylacetate phase is dried and concentrated. The residue is dissolved in 10 ml dioxane, 10 ml of 1N sodium dihydrogen phosphite solution and 3 ml of 33% formaldehyde solution added and the mixture warmed for 30 minutes at 65°. The pH is then adjusted to 11 with 1N sodium hydroxide and extraction with chloroform is carried out three times.

The organic phase is dried and concentrated on a rotary evaporator and the residue dissolved in 5 ml of trifluoroacetic acid, mixed after 7 minutes with 100 ml of diethyl ether and the precipitate filtered off under suction and washed with ether. The product is dissolved in 5 ml of water and converted to the sulphate in a column with IRA 401 S (sulphate-form). $R_f=0.30$ (in chloroform/methanol/30% ammonia=70/26/9).

H-NMR, characteristic signals: 1,38 s,3H;2,7 dd,$J_1=14$,$J_2=3,5$,1H; 2,97 s,3H;2,99 s,6H;5,18 d,J=3,6,1H;5,88 d,J=3,6,1H.

The required starting materials are prepared as follows:

(A)

3,2′,6′,3″-Tetra-N-tert.butoxycarbonyl-1-desamino-1-nitrogengentamicin $C_2$ (for example 1)

To a solution of 17 g of 3,2′,6′,3″-tetra-N-tert.-butoxycarbonylgentamicin $C_2$ and 3.4 g 3-tert.-butyl-4-hydroxy-5-methylenephenylsulphide in 750 ml of 1,2-dichloroethane are added whilst boiling 34 g of 3-chloroperbenzoic acid in solid form. After 30 minutes the solution is concentrated on a rotary evaporator and the residue triturated with 20% $KHSO_3$, saturated $NaHCO_3$ and water and chromatographed over silica gel (ethylacetate/hexane=3/2). The substance with $R_f=0.17$ (dichloromethane/methanol=20/1) is isolated.

(B)

3,2′,6′,3″-Tetra-N-tert.-butoxycarbonnyl-1-desamino-1-nitrogentamicin $C_{1a}$ (for example 2)

A mixture of 50 g potassium permanganate and 125 g potassium dihydrogenphosphate in 0.5 liter of water is brought to 75° and 25 g of 3,2′,6′,3″-tetra-N-tert.-butoxycarbonylgentamicin $C_{1a}$ dissolved in 0.5 liter of acetone added in one gush. The mixture is refluxed for 3 minutes and poured into ice-water containing 150 g of sodium hydrogensulphite. The manganese dioxide is filtered off and the solution extracted with chloroform. After drying, the organic phase is concentrated on a rotary evaporator and the residue chromatographed over silica gel with ethylacetate/hexane=3/2. A colourless foam is obtained $R_f=0.16$ (dichloromethane/methanol=20/1).

The following compounds may be obtained analogously:
3,2′,6′,3″-Tetra-N-tert.-butoxycarbonyl-1-desamino-1-nitrogentamicin $C_1$.$R_f=0.74$ (dichloromethane/methanol=9/1)
3,2′,6′,3″-Tetra-N-tert.-butoxycarbonyl-1-desamino-1-nitrogentamicin $C_{2a}$.$R_f=0.17$ (dichloromethane/methanol=20/1)

We claim:
1. A compound which is either a base of formula I

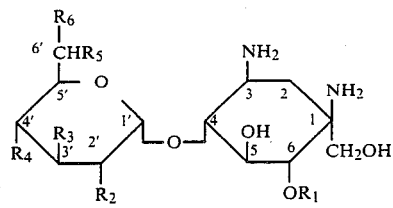

wherein $R_1$ represents hydrogen or a group of formula

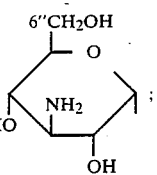

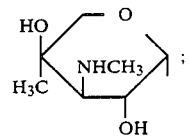

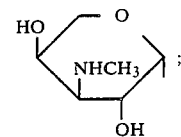

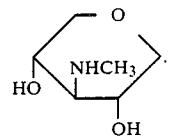

$R_2$ represents hydroxy or amino, $R_3$ represents hydrogen or hydroxy, $R_4$ represents hydrogen or hydroxy, $R_5$ represents amino, methylamino, dimethylamino or, when $R_2$ represents amino also hydroxy and $R_6$ represents hydrogen or methyl; or a chemotherapeutically acceptable acid addition salt thereof.

2. 1-C-Hydroxymethylgentamicin $C_2$ in free base form or in the form of an acid addition salt.

3. A compound according to claim 2 in the form of its pentahydrochloride or sulphate.

4. A pharmaceutical composition suitable for use as an antibacterially active antibiotic, comprising an antibacterially-effective amount of a compound of claim 1 with a chemotherapeutically acceptable diluent or carrier.

5. A method of combatting bacteria comprising administering to a subject in need of such treatment an effective amount of a compound of claim 1.

6. A compound of the formula III

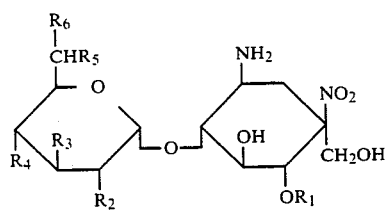

wherein $R_1$ represents hydrogen or a group of formula

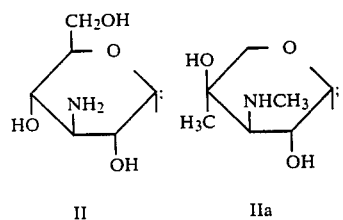

$R_2$ represents hydroxy or amino,
$R_3$ represents hydrogen or hydroxy,
$R_4$ represents hydrogen or hydroxy,
$R_5$ represents amino, methylamino, dimethylamino or, when $R_2$ represents amino also hydroxy and
$R_6$ represents hydrogen or methyl; any amino groups of which may be in protected or unprotected form.

7. A compound of the formula IV

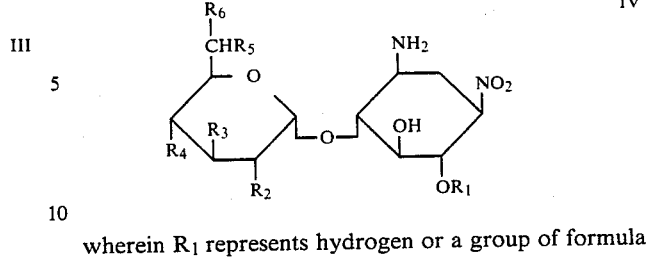

wherein $R_1$ represents hydrogen or a group of formula

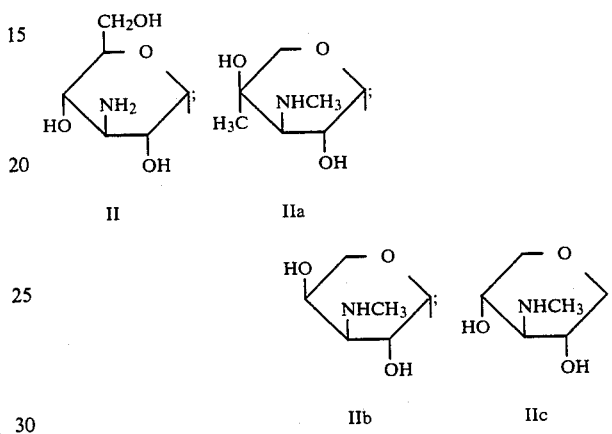

$R_2$ represents hydroxy or amino,
$R_3$ represents hydrogen or hydroxy,
$R_4$ represents hydrogen or hydroxy,
$R_5$ represents amino, methylamino, dimethylamino or, when $R_2$ represents amino also hydroxy and
$R_6$ represents hydrogen or methyl; any amino groups of which may be in protected or unprotected form.

8. The compound according to claim 3 which is in the form of its pentahydrochloride.

9. The compound according to claim 3 which is in the form of its sulfate.

10. A compound according to claim 1 wherein:
$R_1$ represents a group of formula IIa,
$R_2$ represents amino,
$R_3$ and $R_4$ represent hydrogen,
$R_6$ represent hydrogen or methyl and
$R_5$ represents amino, methylamino or dimethylamino.

* * * * *